(12) United States Patent
Wilcox et al.

(10) Patent No.: US 6,706,839 B1
(45) Date of Patent: Mar. 16, 2004

(54) CHEMICAL PARTITIONING AGENTS AND METHODS OF USING SAME

(75) Inventors: Craig Stephens Wilcox, Pittsburgh, PA (US); Jaemoon Yang, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/913,231

(22) PCT Filed: Feb. 10, 2000

(86) PCT No.: PCT/US00/03523

§ 371 (c)(1),
(2), (4) Date: Dec. 10, 2001

(87) PCT Pub. No.: WO00/47031

PCT Pub. Date: Aug. 17, 2000

Related U.S. Application Data
(60) Provisional application No. 60/119,404, filed on Feb. 10, 1999.

(51) Int. Cl.$^7$ ............................................... C07B 63/02

(52) U.S. Cl. ....................... 526/346; 548/240; 560/128; 560/129; 560/138

(58) Field of Search ........................ 526/346; 548/240; 560/128, 129, 138

(56) References Cited

U.S. PATENT DOCUMENTS

| | | |
|---|---|---|
| 5,082,955 A | 1/1992 | Lemaire et al. |
| 5,202,504 A | 4/1993 | Toda |
| 5,276,214 A | 1/1994 | Toda |
| 5,334,776 A | 8/1994 | Toda |
| 5,395,985 A | 3/1995 | Toda |
| 5,463,082 A | 10/1995 | Horvath et al. |
| 5,498,810 A | 3/1996 | Bogdan et al. |
| 5,516,957 A | 5/1996 | Dandekar et al. |
| 5,777,121 A | 7/1998 | Curran et al. |
| 5,854,370 A | 12/1998 | Yokota et al. |

FOREIGN PATENT DOCUMENTS

| | | |
|---|---|---|
| JP | 05051328 | 3/1993 |
| JP | 05301864 | 11/1993 |
| JP | 06080605 | 3/1994 |
| JP | 06166659 | 6/1994 |
| JP | 07010822 | 1/1995 |
| JP | 08081398 | 3/1996 |
| JP | 08259552 | 10/1996 |
| JP | 09012482 | 1/1997 |
| JP | 9-19310 A2 | 8/1997 |
| WO | WO 00/21368 | 4/2000 |

OTHER PUBLICATIONS

Negishi, E–I et al."Synthesis of Biaryls Via Palladium–Catalyzed Cross Coupling: 2–Methyl–4'–Nitrobiphenyl"; *Organic Syntheses*; 1988, pp. 67–74.

Booth, R. et al.; "Polymer–Supported Quenching Reagents for Parallel Purification"; *J. Am. Chem. Soc.*, 1997, 119, pp. 4882–4886.

Gravert, D. et al.; "Organic Synthesis on Soluble Polymer Supports: Liquid–Phase Methodologies"; *Chem. Rev.*, 1997, 97, pp. 489–509.

Hammond, G. et al.; "Mechanisms of Photochemical Reactions in Solution. XXII. Photochemical cis–trans Isomerization"; *J. Am. Chem. Soc.*; 1964; 86, pp. 3197–3217.

Han, H. et al.; "Liquid–Phase Combinatorial Synthesis"; *Proc. Natl. Acad. Sci.*, vol. 92, Jul. 1995, pp. 6419–6423.

Herkstroeter, W. et al.; "Mechanisms of Photochemical Reactions in Solution. XXXIX. Study of Energy Transfer by Kinetic Spectrophotometry"; *Journal of the American Chemical Society*, vol. 88, No. 21, Nov. 4, 1966, pp. 4769–4780.

Kim, R. et al.; "Dendrimer–Supported Combinatorial Chemistry"; *Proc. Natl. Acad. Sci.* vol. 93, Sep. 1996, pp. 10012–10017.

Studer, A. et al.; "Fluorous Synthesis: A Flourous–Phase Strategy for Improving Separation Efficiency in Organic Synthesis"; *Science*, vol. 275, Feb. 1997, pp. 823–826.

Uenishi, J. et al.; "A General and Convenient Synthetic Method of Geometrically Pure (Z)–1–Bromo–1–alkenes"; *Tetrahedron Letters*, vol. 37, No. 37, 1996, pp. 6759–6762.

PCT International Search Report, International Application No. PCT/US00/03523 dated Jul. 19, 2000.

Lin, Y. et al.; "Photo–Asymmetric Synthesis of Helicenes in Liquid Crystals"; *Mol. Cryst. Kiq. Cryst.*, 1997, vol. 301, pp. 267–282.

Spatz, S.; "Thermal Decarboxylation of Diaryl Fumarates to Stilbenes"; *J. Org. Chem.*, 1961, vol. 26, pp. 4158–4161.

Johnson, T.B. et al. Researches on Amines. IV. The Alkylation and Hydrolysis of Aliphatic Sulfonamides. A New Synthesis of Sarconsine. J. Am. Chem. Soc. 1914; 372–385.

Zapio, O. et al. Photochemically Induced Modification of Polymer Dispersed Liquid Crystals with Photochromic Stilbene. Photoreactions in Liquid Crystals (Part 8). Mol. Cryst. Liq. Cryst. 1992; 213: 153–161.

Curran, D.P. et al. Stille Couplings with Fluorous Tin Reactants: Attractive Features for Preparative Organic Synthesis and Liquid–Phase Combinatorial Synthesis. J. Org. Chem. 1996; 61(19): 6480–81.

Gilman, H. et al. Cleavage of Symmetrically Substituted Disilanes by Lithium in Tetrahydrofuran. J. Am. Chem. Soc. Feb. 5, 1958; vol. 80, 608–611.

(List continued on next page.)

Primary Examiner—Richard L. Raymond
Assistant Examiner—Thomas McKenzie
(74) Attorney, Agent, or Firm—Reed Smith LLP (57) ABSTRACT

The present invention is directed to partitioning agents and methods of using same to effectuate separation of a reactant, intermediate product, and/or final product from a reaction mixture while minimizing the need for traditional separation or isolation techniques.

6 Claims, 4 Drawing Sheets

OTHER PUBLICATIONS

Hammond, G.S. et al. Mechanisms on Photochemical Reactions in Solution. XXII. Photochemical cis–trans Isomerization. J. Am. Chem. Soc. 1964, Aug. 20, 1964; 3197–3217.
Moussebois, C. et al. A method of cis, trans–isomerization of non–conjugated olefins without double–bond migration. J. Chem. Soc. (C). 1966; 260–64.
Sauer, J. et al. Einfluss Von Lewis–Säauren auf das endo–exo–verhaltnis bei diels–alder–additionen des cyclopentadiens. Tet. Lett. 1966; 7: 731–6.
Kobuke, Y. et al. The endo selectivities of some methyl–substituted dienophiles in Diels–Adler reactions with cyclopentadiene. J. Am. Chem. Soc. Nov. 4, 1970; 92(22): 6548–53.
Vedejs, E. et al. Olefin inversion by the phosphorus betaine method. J. Amer. Chem. Soc. Aug. 11, 1971; 93(16): 4070–2.
Feutrill, G.I. et al. Reaction with Thioethoxide Ion in Dimethylformide. I. Selective Demethylation of Aryl Methyl Ethers. Aust. J. Chem. 1972; 25:1719–29.
Wismonski–Knittel, T. et al. Temperature dependence of photoisomerization. Part VIII. Excited–state behavior of 1–naphthyl–2–phenyl– and 1,2–dinaphthyl–ethylenes and their photocyclisation products, and properties of the latter. J.C.S. Perkin II. 1974; 1930–40.
Bridges, A.J. et al. A method of Olefin Inversion via Phosphine Oxides. J.C.S. Comm. 1974; 142–143.
Still, W.C. Conjugate Addition of Trimethylsilyllithium. A Preparation of 3–Silyl Ketones. J. Org. Chem. 1976; 41(18): 3063–64.
Calo, V. et al. 3–Methyl–2–selenoxobenzothiazole, a new reagent for the stereospecific deoxygenation of epoxides and the desulfurization of episulfides into olefins. Synth. Comm. Mar. 1976; 200–201.
Gascoyne, J.M. et al. Fluorine–19 nuclear magnetic resonance studies of aromatic compounds. Part 5. Transmission of substituent effects across two aromatic rings connected by C–C and –C–linkages. J.C.S. Perkins II. 1977; 1051–57.
Hassner A. et al. Direct room temperature esterification of carboxylic acids. Tet. Lett. 1978; 46: 4475–78.
Sonnet, P. E. Olefin Inversion. Tetrahedron Report No. 77. 1980; 557–604.
Lipshutz, B.H. et al. Chemistry of higher order, mixed organocuprates. 1. Substitution reactions at unactivated secondary centers. J. Am. Chem. Soc. 1981; 103(25): 7672–7674.
Lapouyade R. et al. Photocyclization of 1,2–diaryllethylenes in primary amines. A convenient method for the synthesis of dihydro aromatic compounds and a means of reducing the loss of methyl groups during the cyclization of o–methyl-stilbenes. J. Org. Chem. 1982; 47(7): 1361–64.
De Lucchi, O. et al. (Z) and (E)–1,2–Bis(phenylsulfonyl) ethylenes as synthetic equivalents to acetyldene as dienophile. J. Org. Chem. 1984; 49(4): 596–604.
Martin, M.G. et al. Epoxides as alkene protecting groups. A mild and efficient deoxygenation. Tet. Lett. 1984; 25(3): 251–54.
Somers, J.B.M. et al. Base–induced proton tautomerism oin the primary photocyclization product of stilbenes. J. Am. Chem. Soc. 1985; 107(5): 1387–94.
Nishimura, J. et al. Coupling reaction of grignard reagents with α, w–dibromoalkanes in the presence of copper(I) bromide–HMPA: Preparation of α, w–Bis(vinylary)alkanes. Bull. Chem. Soc. Jpn. Jun 1986; 59(6): 2035–37.

Annuziata, R. et al., Stereoselectivity of intramolecular nitrile oxide cycloadditions to Z and E chiral alkenes. J. Org. Chem. 1987; 52(21): 4674–81.
Wong, H. et al. Stereospecific deoxygenation of epoxides to olefins. Heterocycles. 1987; 26(5): 1345–82.
Khanapure S. et al. Preparation of novel 4–substituted 6–methoxy–, 6,7–dimethoxy–, and 6,7–(methylenedioxy)isochroman–3–ones. J. Org. Chem. 1990; 55(5): 1471–75.
Murthy, N. et al. Diels–Alder reactions catalyzed by zeolites. Synth. Comm. 1991; 21(6): 783–91.
Osterby, B. et al. Photochromic Sunglasses: A patent–based advanced organic synthesis project and demonstration. J. Chem. Ed. May 1991; 68(5):424–425.
Ali, M. A. et al. New Method for Isomerization of (Z)–Stilbenes into (E)–Isomers Catalyzed by Diaryl Disulfide. Chem. Pharm. Bull. 1992; 40(10); 2842–44.
Kakishita, T. et al. Synthesis and NMR Study of 9'–substituted Spiroindolinonaphthoxazine Derivatives. J. Het. Chem. Dec. 1992; 29: 1709–1715.
Murray, R.W. et al. Dioxiranes. 20. Preparation and properties of some new dioxiranes. J. Am. Chem. Soc. 1992; 114(4): 1346–1351.
Tardieu, P. et al. 92. Synthèse et propriétés photochromiques de 1,3–dihydrospiro 2H–indole–2,3'[3H]pyrimido[5,4–f] benzoxazines et de 1,3–dihydrospiro 2H–indole–2,7'–[7H0thiazolo 5,4–f][1,4]benzoxazines. Helv. Chim. Acta. 1992; 75:1185–1197.
Maruoka, K. et al. Asymmetric Diels–Alder reaction of cyclopentadiene and methyl acrylate catalyzed by chiral organoaluminum reagents. Bull. Chem. Soc. Jpn. Dec. 1992; 3501–03.
Cativiela, C. et al. On the role of hexafluoroisopropanol in Diels–Alder reactions of acid–sensitive reagents. Can. J. Chem. 1994; 72: 308–311.
Forman, F. W. et al. Solid–phase synthesis of biaryls via the stille reaction. J. Org. Chem. 1995; 60(3): 523–528.
Miyazawa, T. et al. Selective isomerization of cis–Stilbene by non–resonant two–photon excitation. Chem. Lett. 1995; 217–18.
Moustrou, C. et al. Synthesis of thiophene–substituted spiropyrans and spirooxazines, precursors of photochromic polymers. Helv. Chim. Acta. 1995; 78:1887–1894.
Yang, D. et al. Epoxidation of olefins using methyl(trifluoromethyl)dioxirane generated in Situ. J. Org. Chem. 1995; 60(12): 3887–89.
Balkenhohl, F. et al. Combinatorial synthesis of small organic molecules. Angew. Chem. Int. Ed. 1996; 35: 2288–2337.
Gordon, E.M. et al. Strategy and tactics in combinatorial organic synthesis. Applications to drug discovery. Acc. Chem. Res. 1996; 29(3): 144–154.
Hermkens, P. et al. Solid–phase organic reactions: a review of the recent literature. Tetrahedron Report No. 394. 1996; 52(13): 4527–4554.
Thompson, L. A. et al. Synthesis and Applications of Small Molecule Libraries. Chem. Rev. 1996; 96: 555–600.
Yang, D. et al. A $C_2$symmetric chiral ketone for catalytic asymmetric epoxidation of unfunctionalized olefins. J. Am. Chem. Soc. 1996; 118(2): 491–492.
Bearpark, M.J. et al. Cooperating rings in cis–stilbene lead to an $S_0/S_1$ conical intersection. J. Phys. Chem. May 22, 1997; 101(21): 3841–47.

Du, X. et al. Synthesis of benzofuran derivatives on solid support via $SmI_2$–mediated radical cyclization. J. Org. Chem. 1997; 62(17): 5678–79.

Gravert, D.J. et al. Organic Synthesis on Soluble Polymer Supports: Liquid–Phase Methodologies. Chem. Rev. 1997; 97: 489–510.

Herrmann, W. et al. Supramolecular control of the photochemistry of stilbenes by cyclodextrins. Chem. Comm. 1997; 1709–10.

Ichimura, et al. Macrocyclic Amphiphiles. 1. Properties of Caliz[4]resorcinarene Derivatives Substituted with Azobenzenes in Solutions and Monolayers. Langmuir. 1997; 6780–86.

King, N.R. et al. Effect of media polarity on the photoisomerization of substituted stilbene, azobenzene and imine chromophores. J. Mater. Chem. 1997; 7(4): 625–30.

Plunkett, M. J. et al. Geranium and silicon linking strategies for traceless solid–phase synthesis. J. Org. Chem. 1997; 62(9): 2885–93.

Studer, A. et al. Fluorous synthesis: A flourous–phase strategy for improving separation efficiency in organic synthesis. Science. Feb. 1997; 275: 823–6.

Waga, M. et al. Excitation wavelength dependence of the Z → E one–way isomerization of 4–halostilbene radical cations in excited states. Chem. Phys. Lett. 1997; 265: 277–82.

Burns, C.J. et al. Nanomolar inhibitors for two distinct biological target families from a single synthetic sequence: a next step in combinatorial library design? Angew. Chem. Int. Ed. 1998; 37: 2848–50.

Curran, D.P. Strategy–Level Separations in Organic Synthesis: From Planning to Practice. Angew. Chem. Int. Ed. 1998; 37: 1174–1196.

Grant, D.J.W. et al. Chapter II: Solubility, Intermolecular Forces, and Thermodynamics, *Solubility Behavior of Organic Compounds:* John Wiley & Sons, New York, NY 1990; 12–88.

Grant, D.J.W. et al. Chapter III: Activities of Solutes, Selection of Standard State and Henry's Law Constants, *Solubility Behavior of Organic Compounds.* John Wiley & Sons, New York, NY 1990; 89–133.

Hildebrand, J.H.; Scott, R.L. Chapter 2: Thermodynamic Relations, *Regular Solutions,* Prentice–Hall, Englewood Cliffs, NJ, 1962; 8–25.

Hildebrand, J.H.; Scott, R.L. Chapter 6: Intermolecular Forces, *Regular Solutions,* Prentice–Hall, Englewood Cliffs, NJ, 1962; 66–87.

CHEMICAL PARTITIONING AGENTS AND METHODS OF USING SAME

This application claims the benefit of Provisional Application No. 60/119,404, filed Feb. 10, 1999.

FIELD OF THE INVENTION

The present invention relates generally to agents useful in partitioning and/or purification of reactants, intermediate products, and final products from a phase as well as methods of using partitioning agents to selectively separate active agents (either reactant or product) from a phase. The present invention may also be described as being directed to chemical product isolation, separation, phase transfer, and/or purification as well as agents or compounds useful therefor.

BACKGROUND OF THE INVENTION

An important part of any synthesis or natural product isolation procedure is the separation of a desired compound from contaminants. This step is often the most labor intensive, energy demanding, environmentally abusing, and expensive part of a chemical synthesis or chemical manipulation. Contaminants may include solvents, reaction byproducts, catalysts, reagents, and any other material not required for, or undesirable in, further uses of the product. Both fine chemical synthesis and larger scale chemical production involve at least two essential activities—chemical reaction to create the product, and separation (most often for purification purposes) of the product by removing contaminants.

Separations generally rely on phase changes or phase transfers. Distillation, sublimation, solvent evaporation, chromatography, acid-base extraction, solid-solid and solid-liquid extraction, and recrystallization are examples of traditional means of product isolation.

A more recent and currently popular approach to product isolation is based on solid-phase synthetic principles. Generally, solid phase synthesis involves attaching a reactant to an insoluble substrate and allowing reagents to react with the reactant at the surface of the solid. Often beads composed of polymers are used for this process. This method allows the use of large excesses of reagents and catalysts because product separation is achieved by filtration or washing of the solid support. High chemical conversion can be achieved when excesses of reagents are used. However, solid phase synthesis does not have universal applicability. One disadvantage of solid phase synthesis is that reactions at the solid-liquid interface are not always readily controlled. Additionally, not all chemical reactions are compatible with this method, and since solid phase separation is substantially heterogeneous, the use of solid phase synthesis runs contrary to a more preferred homogenous reaction mixture.

Homogeneous reaction mixtures are desirable because reaction conditions can be reliably controlled. A primary disadvantage of homogeneous reactions, and one that solid phase synthesis attempts to avoid, is that contaminants are in the same phase and intimately mingled with desired products or intermediate materials. Products, whether they be final or intermediate stage products, have traditionally been precipitated by removing solvent or by changing solvent, and by covalent or ionic modifications of the product through addition of more chemicals (for example, acids, bases, or metals). Changes in solubility caused by salt formation or protonation or deprotonation can support liquid-liquid extraction approaches to product separation.

Yield, feasibility, and practicality of nearly every reaction is limited by the ability to separate and recover pure product from the reaction mixture. Thus, synthesis and separation are inseparable. Advances in the field of separation have enabled modern synthetic chemists to contemplate and then synthesize molecules of remarkable complexity. At the same time, the power of modern separations has instilled a certain degree of complacency. On the process-chemistry front, one is expected not only to synthesize the desired compound, but to synthesize it cheaply, efficiently, and safely. Furthermore, the advent of combinatorial chemistry has resulted in an expectation that everything can be synthesized quickly. Synthetic chemists have begun to formulate strategic plans for separation at the beginning of a synthesis. In these plans separation dictates synthesis and molecules in the final reaction mixture are designed to virtually separate themselves when processed in a purification stage. These plans rely on relatively simple workup techniques such as evaporation, extraction, and filtration.

Four phases are commonly used in standard laboratory separation methods: a gas phase, a solid phase, and two liquid phases—organic and aqueous. A third liquid phase known as a "fluorous" phase has recently found applicability in organic synthesis. Among the phase separation techniques, liquid-liquid extractions play an important role in the purification of organic compounds. These extractions are almost always conducted with an organic solvent and water. Most frequently, they are used to separate organic compounds from inorganic compounds. A less frequent but still important application of organic-water extractions is an acid-base extraction. Yet another common technique used for separation is chromatography. Chromatographic methods of purification are immensely important, yet they are also expensive and time consuming. A recent review of issues and approaches to product isolation and extraction is provided in "Strategy-Level Separations in Organic Synthesis: From Planning to Practice," D. P. Curran, Angewandte Chemie Int'l Ed. Engl., 1998, v 37, 1174, which is hereby incorporated by reference thereto in its entirety.

SUMMARY OF THE INVENTION

The present invention is directed to a separation technique and agents useful therefor. As will be described more fully herein, the present invention allows for selective isomerization of a chemical moiety removably attached to a product or intermediate for selective separation of product or the intermediate by phase change or transfer.

Specifically, compounds described herein comprise a reactant isomer functionalized for attachment to a reactant molecule, the reactant isomer capable of being isomerized into a separating isomer, the separating isomer having a different solubility than the reactant isomer. The compound or compounds generally are of the following formula wherein R11 and R12 are each independently the same or different, a hydrogen, a halide, OR, OH, OOH, OOR1, SR1, CN, NC, NR1R, a linear or branched alky group, an aryl group, a phenyl group, a substituted aryl, a substituted phenyl group, or other common functional group.

Another embodiment of the present invention is a compound of the following formula wherein L is a linking group, the linking group being capable. of isomerization and R1, R2, R3, R4, R5, R6, R7, R8, R9, and R10 are, each independently, the same or different, a halide, OR, OH, OOH, OOR1, SR1, CN, NC, NR1R, a linear or branched alky group, an aryl group, a phenyl group, a substituted aryl, a substituted phenyl group, or other common functional group. Further, it is preferable that the reactant isomer be a cis-alkene and the separating isomer be a trans alkene. The separating isomer may also be a geometrical isomer, a stereoisomer and/or a structural isomer.

A method of separating a desired product from a reaction mixture is also disclosed wherein the method is comprised of covalently linking a separating agent to a reactant molecule, reacting the so formed reactant molecule to form a product with the separating agent being attached to the product, isomerizing the separating agent to thereby form a separable form of the product, and separating the product from the reaction mixture. The method further includes the step of cleaving the separating agent from the product to thereby form a purified product. Isomerization may occur through geometrical isomerization, stereoisomerization, and/or structural isomerization. Preferably, in this embodiment, the modified reactant molecule may be selectably transferred from one phase (e.g., hydrophobic) to another (e.g., hydrophilic) by isomerization.

The phase partitioning agent may also be of the general formula:

wherein L is a linking group, the linking group being capable of isomerization and R1, R2, R3, R4, R5, R6, R7, R8, R9, and R10 are, each independently, the same of different, a halide, OR, OH, OOH, OOR1, SR1, CN, NC, NR1R, a linear or branched alky group, an aryl group, a phenyl group, a substituted aryl, a substituted phenyl group, or other common functional group. Some useful phase partitioning agents are represented below:

a)

-continued g)

Another aspect of the present invention is a method of partitioning a reactant from a phase comprising isomerizing a precipiton covalently linked to the reactant. The step of isomerizing the precipiton may include adding a chemical isomerizing agent and in a preferred embodiment irradiating the precipiton. In addition the reactant may have a plurality of precipitons attached to the reactant with each of the plurality of precipitons individually and selectively isomerizable.

The term "reagent" as used herein refers to a chemical entity that is required for a reaction but contributes either an invariant piece or no piece to the products of a synthesis. As used herein, the term "reagent" includes a catalyst or any agent that is necessary to the chemical reaction but is itself substantially unchanged during the chemical reaction, whether or not it is used in substoichiometric quantities.

The term "reactant" as used herein in connection with synthesis refers generally to a type of molecule that contributes a variable piece to the products of a synthesis. The distinction between the terms "reactant" and "reagent" in "common" (non-combinatorial) organic syntheses is vague, but those skilled in the art often refer to a reaction component as a reagent if it contributes no piece, a rather small piece, or a piece without carbon atoms therein to the target product.

DETAILED DESCRIPTION OF THE PREFERRED EMBODIMENTS

The present invention provides a novel approach to chemical product isolation and purification. Based on different solubilities between pairs or groups of isomers (e.g., geometrical, stereo, or structural isomers) can have very different solubilities.

In the present invention, a chemical moiety is preferably introduced into a synthesis via linkage to any component of a chemical reaction, preferably a reactant such as a starting material or intermediate product. For convenience this chemical moiety is referred to herein as a "precipiton." The term "precipiton" as used herein means any group of atoms (molecule or molecular fragment) that is purposefully added to a reactant molecule in order to facilitate phase transfer, separation or isolation of the intermediate or final product. The term "precipiton" is used herein because the separation or isolation is usually precipitation based isolation. However, the term "precipiton" is by no means to be construed in such a limited sense. The precipitons of the present invention preferably include an agent, which when isomerized, causes or initiates a phase transfer. This phase transfer characteristic preferably allows phase transfer of the molecule to which it is attached (conjugate system). The phase transfer is due to variable solubilities of respective groups of isomers. The present invention is preferably directed to precipitons that are designed to be soluble under the conditions of the reaction and to become insoluble after isomerization. Stereoisomerization is the preferred isomerization technique because no atoms are added or removed from the precipiton.

One advantage of the present invention is the minimization of the need for chromatography, distillation, extraction, or other traditional means of product isolation are minimized and often eliminated. Another advantage of the present invention is that an excess of reagents (to assure complete reaction progress) can be used in a reaction system with a minimal work-up comprised of the reaction mixture to a phase transfer initiator mechanism, for example, light (e.g., ultraviolet radiation) or a simple reagent, to induce precipitation of only the target molecule (e.g., depending on the stage of the work-up a reactant-precipiton complex). As will be further detailed herein, the use of the precipitons and/or the methods of the present invention in reactions and other bimolecular processes have resulted in products being isolated in greater than 95% purity—without recourse to extraction or chromatographic methods. This present invention is useful in small and medium scale chemical syntheses and in large volume chemical production. The methods described herein are easily automated and can be incorporated into modern robotic approaches to parallel synthesis.

The most preferable phase transfer agents are isomerizable precipitons which afford high solubility of the attached reactant, but yet have low chemical reactivity. After isomerization, the precipiton preferably has a different, preferably very low, solubility in the reaction solvent. This change in solubility may arise from changes in the inter-precipiton attractive forces and/or changes in precipiton-solvent interactions. For example, a change in geometry may lead to a change in dipole moment, causing aggregation of the more polar species that result from such isomerization. Also, changes in surface area of the precipiton may also affect inter-precipiton attraction, because a change in surface area influences both solute-solvent and solute-solute interactions. Isomerization may also lead to exposure of hydrogen bonding groups and lead to alternative non-covalent association of precipitons. The present invention is not to be limited to these approaches or to the above-described changes in solubility. Any precipiton in which geometrical change results in a change in phase partitioning is within the scope of the present invention. Isomerization can be induced by light, by heat, or by added catalysts. The present invention also embodies a method of selective isomerization of the precipiton which leads to a change in reactivity to promote salt formation or complexation to assist in phase separation. For example, the acidity or basicity of the reactants may be modified by isomerization in such a way as to improve phase separation and isolation of product.

Although certain precipitons are specifically described herein for illustrative purposes, general guidelines can be established to optimize precipiton design. Solubility of a solid depends on the activity coefficient of the solute in the solvent and the activity of the solute in the solid state. Two references that generally encompass this field are: (1)

Hildebrand, J. H.; Scott, R. L. "Regular Solutions", Prentice-Hal, Englewood Cliffs, N.J., 1962; and (2) Grant, D. J. W.; Higuchi, T. "Solubility Behavior of Organic Compounds", John Wiley and Sons, New York, N.Y., 1990. Both of these references are hereby incorporated by reference thereto in their entirety.

The solubility of a solid can be related to activity in the solid and the activity coefficient in the solution as follows:

$$S = a/g$$

Here solubility (S) is expressed as mole fraction present in the saturated solution, a is activity in the solid, and g is the activity coefficient in the solution. A preferred precipiton in its higher solubility form relies on isomerization to induce a change that will decrease a and increase g, and thereby convert the precipiton to a lower solubility form and favor precipitation. In cases of phase separation, useful changes in solubility may be in either direction, increasing or decreasing solubility in the medium (phase) or origin. Specific applications will define the desired or expected concentration of the soluble form and will provide a guide to the magnitude of the change that is needed.

To precipitate a solute, it is necessary to diminish S. Therefore changes that decrease activity in the solid (in other words, make it less ideal through increasing intermolecular interactions) or changes that increase the activity coefficient in solution (make it more ideal, decreasing solute solvent interactions) will lead to precipitation.

Larger accessible surface areas, higher symmetry (which affects packing density), tighter packing in the solid, and specific intermolecular interactions in the solid (H-bonding, Keesom and Debye forces) favor precipitation. Crystalline solids may have lower activity and might therefore be preferred on this basis, but amorphous solids have the advantage of greater rates of resolubilization. Therefore both crystalline and amorphous precipitons may find important uses.

The soluble form will usually be nonpolar, therefore relatively facile conversion or change to a polar form is very useful. It will decrease a and have little effect on g. Change to a polarizable form will have less effect, but may be useful. A change leading to a polar more symmetrical form with larger surface area is favorable. It would also be favorable to rely on specific interactions. H-bonds could be intramolecular but be broken on activation. This, too, greatly decreases a.

Some general guidelines in choosing appropriate precipitons follow. If the soluble form of the precipiton is polar and/or polarizable, a change leading to low polarity/polarizability would generally reduce solubility. Therefore a charged asymmetric molecule should become uncharged and symmetric. However, this will also increase activity in solid, in opposition to the desired effect. A molecule that has capacity for intramolecular H-bonding may be considered non-polar. The soluble form would be unable to intramolecularly H-bond. On activation, it -continued $$\text{Z-stilbene} \xrightarrow[\text{reaction conditions}]{\text{Ph}_2\text{S}_2 \text{ (0.2 equiv)},} \text{E-stilbene}$$

| Z-stilbene | E-stilbene | reaction conditions (Z:E); yield (E-stilbene) |
|---|---|---|
|  52Z |  52E | (only E-stilbene); - 11 h (1:19); 79% |

Isomerization

When a solution of (Z)-stilbene (51Z or 52Z) in THF was heated to reflux at 80–90° C. in the presence of Ph$_2$S$_2$ (0.2 equiv) for several hours, the Z to E isomerization occurred smoothly. The reaction was followed by $^1$H NMR (either vinylic protons or NMe$_2$ (51Z), OMe (52Z)). As the reaction proceeded, solid precipitate came out of the solution. Because the (E)-isomers (51E and 52E) are partially soluble in THF, THF solvent was evaporated and the resulting residue was triturated with Et$_2$O. The E-isomer was obtained pure in a 44% (51E) and 79% (52E) yield, respectively without any contamination of either Z-isomer or Ph$_2$S$_2$. The relatively lower yield for 51E is due to the lower Z to E conversion and also to the bigger solubility of 51E in Et$_2$O than 52E in Et$_2$O (Table 26 and 27). In high-boiling solvents such as toluene and p-dioxane, the isomerization was faster than in THF and the reaction was completed in less than 3 h (Table 32). A second catalytic method for isomerization/precipitation employs iodine and a radical initiator, for example dibenzoylperoxide. Irradiation of the cis-alkenes in the presence of 1–50 mol % iodine and 0.1–25 mol % dibenzoylperoxide affords clean isomerization of the cis to trans alkene.

Figure 1:
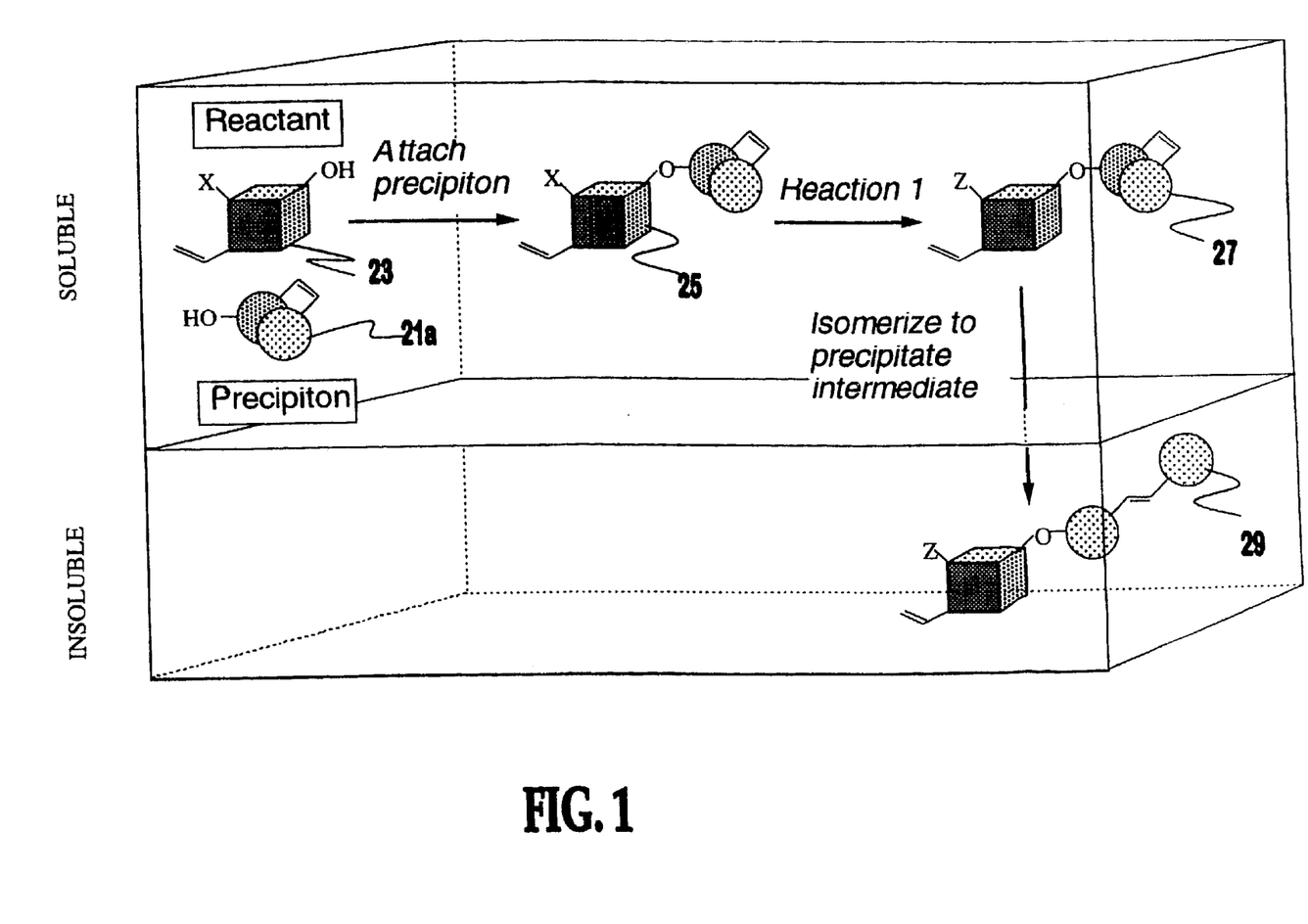
FIG. 1 is a schematic illustration of a typical reaction scheme utilizing a precipiton of the present invention.

FIG. 1 illustrates a simple reaction scheme utilizing a precipiton. The soluble form 21a of a precipiton is shown as being in the same phase as reactant 23. Reactant 23 which is a starting material that bears three functional groups—an alkene, a hydroxyl group, and a reactive group generalized as "X." As illustrated, the OH or hydroxy group is used as an attaching group to precipiton 21a, however, any suitable functional group would suffice as an attachment site. The reactant 23 is attached to the separating agent (precipiton) 21a through their OH groups (as, for example, may occur in ether or ester formation). The conjugate of these two moieties is molecule 25. Molecule 25 may be referred to herein as a reactant-precipiton complex or conjugate or a reactant molecule having a separating agent attached thereto. Reactive group "X" is transformed to "Z" by Reaction 1. The product of this transformation is intermediate-precipiton complex 27. Treatment of intermediate-precipiton complex 27 with a catalyst or with light causes isomerization of the separation agent portion of the intermediate-precipiton complex 27 and results in separation of the product-precipiton conjugate 29 due to a reduced solubility or a change in phase affinity. The separated product-precipiton complex 29 contains the transformed moiety 21b which can be cleaved from the precipiton to afford pure product (not shown).

Figure 2:
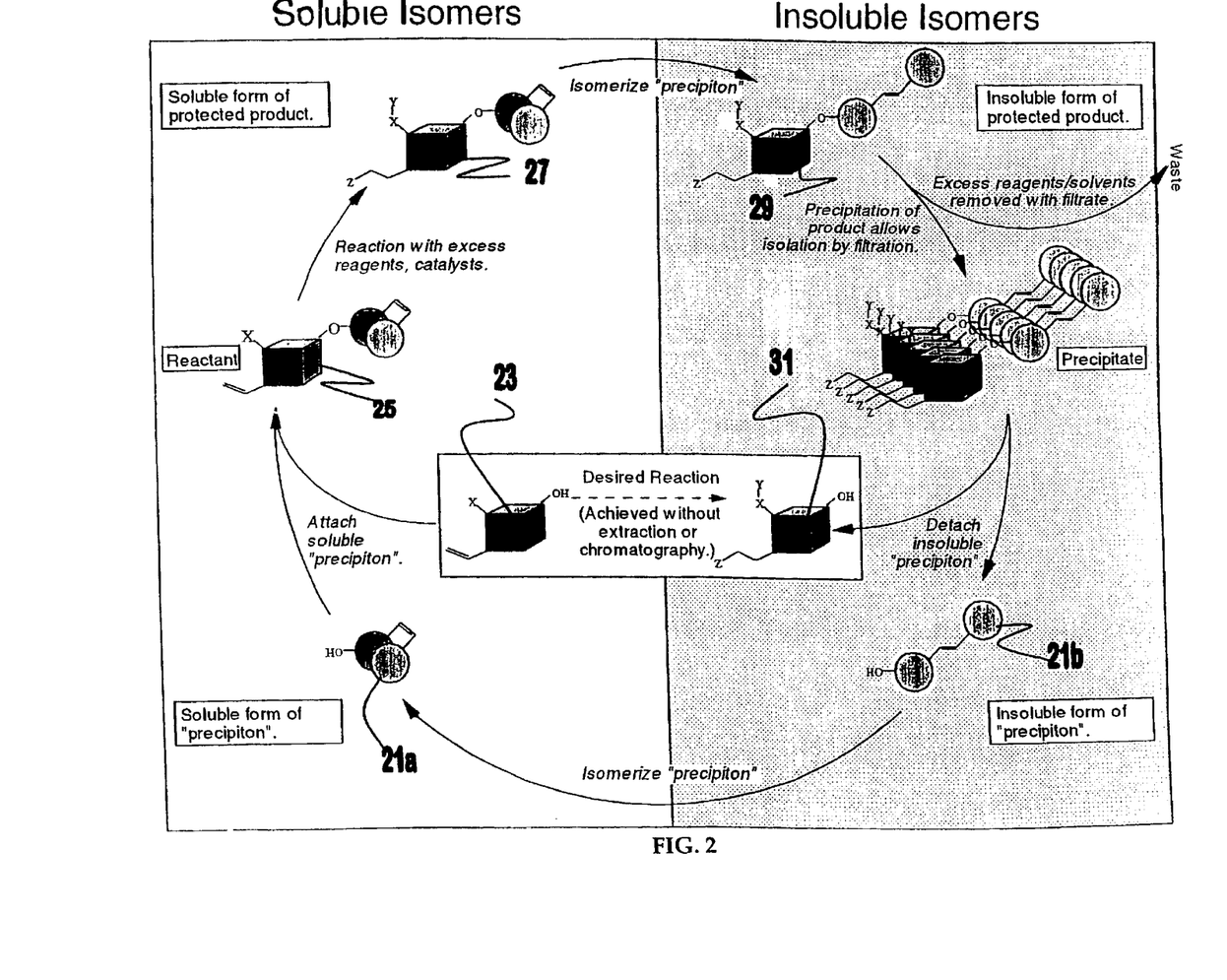
FIG. 2 is a schematic illustration of a reaction scheme wherein the precipiton is regenerated for further use.

FIG. 2 illustrates another aspect of the present invention wherein the precipitons may be recycled. FIG. 2 demonstrates how waste products are separated by filtration from the solid reaction product. The isolated precipitate 31 can be separated from waste products by filtration. The precipitated product-precipiton complex 29 can be worked up so that the separation agent can be isolated (in this case the trans-form 21b of the precipiton) to afford pure product 31 and the insoluble form of precipiton 21b. This insoluble form of precipiton 21 can be rendered soluble by reversing the isomerization to create a more soluble form of the precipiton 21a which may be used again in a reaction.

Figure 3:
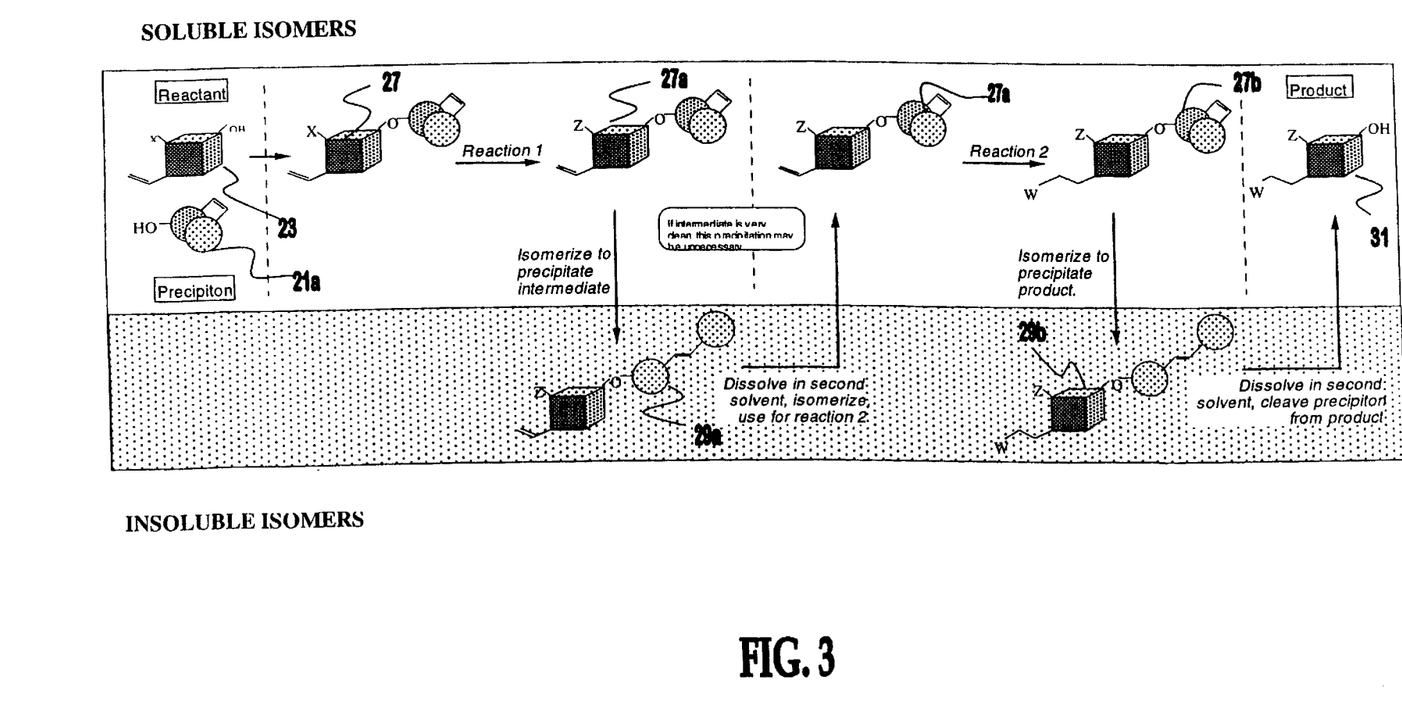
FIG. 3 is a schematic illustration of a more complicated reaction involving a precipiton.

FIG. 3 illustrates another aspect of the present invention wherein the precipiton concept is used in a multi-step process. The first reaction is carried out on a reactant 23 which is attached to the soluble form 21a of precipiton resulting in an intermediate-precipiton complex 27. Intermediate-precipiton complex 27 is then the reactant for reaction 1 wherein the "X" functional group is transformed to a "Z" functional group. This second intermediate-precipiton complex 27a is isomerized resulting in an insoluble intermediate product-precipiton complex 29a. Product-precipiton complex 29a is dissolved in a second solvent and the precipiton portion of 29a is isomerized back into the soluble form of the precipiton and this resolubilized purified form of intermediate-precipiton complex 27a is utilized in reaction 2. Intermediate-precipiton complex 27a is transformed via reaction by addition of the functional group "W" to the alkene of intermediate-precipiton complex 27a resulting in a second intermediate-precipiton complex 27b which is soluble in the reaction phase. The soluble form of the second intermediate-precipiton complex 27b is isomerized to precipitate a second product-precipiton complex 29b. This second product-precipiton complex 29b is then issolved in a second solvent and the precipiton portion of product-precipiton complex 29b is cleaved resulting in product 31 which is easily isolatable from the precipiton (either in the form of soluble precipiton 21a or insoluble precipiton 21b). The reaction process shown in FIG. 3 illustrates the utility of the present invention in a multi-step process whereby the many of the complicated separation or isolation techniques are eliminated due to the selectable control (e.g., through photoismerization) of the precipiton attached to the reactant.

As it turns out, stilbenes appear to be particularly suitable candidate molecules for a precipiton, primarily because of two very attractive properties: facile Z-E isomerization and an intrinsic low solubility of E-isomer. The general features of the reaction scheme are shown below.

This example and specific precipitons or methods or reactions provided herein are meant to further describe the present invention, but are not intended in any way to restrict its scope.

The photoisomerization reaction is preferably executed by irradiation with the use of ultraviolet light generated from UV emission equipment known to those skilled in the art. The material subject to irradiation can be in the form of solution, melt, or solid. Solvent can be employed, and the solvent will generally be one or more organic solvents. There are no particular limitations to the solvent provided that neither photoisomerization nor the practice of the invention are impaired. Suitable solvents for the photoisomerization include hydrocarbons, including aromatic and acyclic hydrocarbons. Examples include the aromatic hydrocarbons toluene and xylene. Halogenated hydrocarbons can be used and examples include halobenzenes such as chlorobenzene. Ethers can be used such as, for example, dioxane and tetrahydrofuran. Alcohols can be used, and examples include alkanols such as the lower-alkanols exemplified by methanol, ethanol, propanol, butanol, pentanol, and hexanol. Ketones can be used including, for example, methyl isobutyl ketone, methyl ethyl ketone, acetone, cyclopentanone, and cyclohexanone. Aprotic polar solvents can be used such as, for example, dimethylsulfoxide, dimethylacetamide, dimethyformamide, and N-methylpyrolidone. Glycols can be used such as, for example, ethylene glycol, propylene glycol, diethylene glycol, dipropylene glycol, ethylene glycol monomethyl ether, and propylene glycol monomethyl ether. Acidic solvents can be used such as, for example, lower alkyl carbonic acids including acetic acid, chloroacetic acid, and butyric acid. The above solvents can be used singly or in a combination.

Suitable irradiation equipment for the photoisomerization reaction is known to those skilled in the art and includes a low-pressure mercury lamp, a high-pressure mercury lamp, a Xenon lamp and lasers such as an excimer laser. The efficiency of the absorption band of the compound and the wave length of emission lines of the light source may be chosen based on criteria commonly known to those skilled in the art. It is therefore preferable to select the light source by matching its UV emission to the wavelength range of the absorption band in ultra-violet and visible regions of the trans-isomer. In general, the region of the wavelength of the emission lines to be utilized is between about 200 nm and about 800 nm, more preferably between about 250 and about 550 nm, even more preferably 300–400 nm, and even more preferably about 350 nm. The photoisomerization can be used to change the solubility of the irradiated compound. That is, isomerization may be used to change the solubility of a compound from soluble to less soluble and vice versa from less soluble to more soluble. Recovered isomerized precipiton may be recycled. Several chemical and photochemical methods are available for transforming E-alkenes to Z-alkenes and Z-alkenes to E-alkenes. These methods, when applied to the recovered material, would provide the soluble precipiton form for reuse. Some isomerizable precipitons can be readily changed from one form to another through irradiation with ultraviolet or visible light. This photon driven switching of solubility in fact is a preferred embodiment of the invention.

Volatile and non-volatile products, and targets that (after cleavage from the precipiton) are liquids, solids, or gases may be prepared by this method. An advantage of the present invention is that the products are isolated in good yield often without resorting to liquid-liquid extraction, chromatography, distillation or recrystallization. Yield of the reactions described here are similar to that obtained using traditional methods, but costs of production as measured by time and materials can be significantly reduced.

In traditional protecting group technologies, no one agent is universally useful for all reactions. In this regard, utilization of the present invention will likely require a family of isomerizable precipitons. The members of this family may differ in chemical reactivity, mechanism of isomerization, and solvent compatibility. Precipitons for aqueous media can be based on the same principles outlined in this invention, and no limitation to solvent is intended or foreseen. Finally, the change in solubility induced by isomerization of a precipiton will obviously lead to changes in partition coefficient in liquid-liquid extraction, and will be relevant to other phase separation-based methods of purification. These changes in wettability and solvent affinity induced by isomerization may also find application in lithography or other technological domains. Several such extensions of the present invention should be obvious to those skilled in chemical and molecular science.

Figure 4:
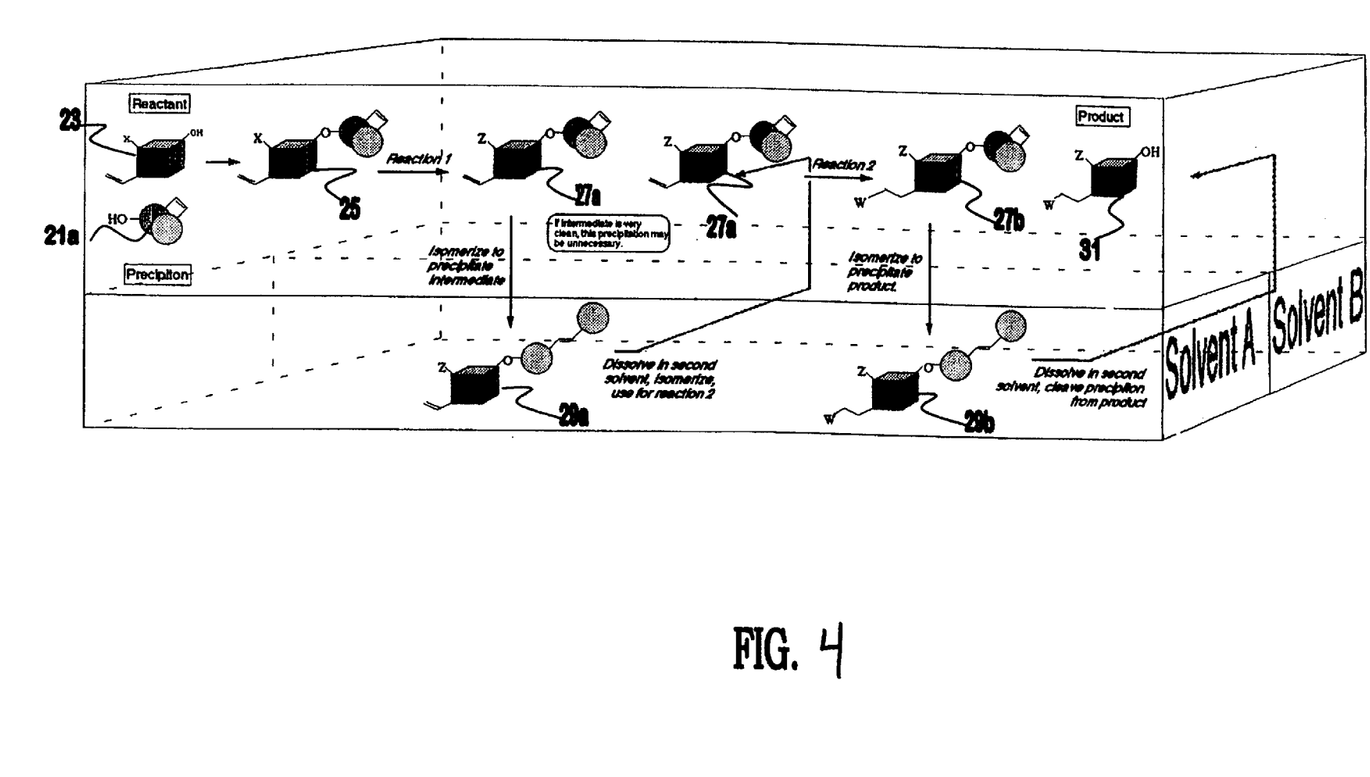
FIG. 4 is a schematic illustration of a biphasic reaction condition utilizing a precipiton of the present invention.

FIG. 4 illustrates in a three-dimensional manner a multi-stage process like that shown in FIG. 3, but with even further potential elimination of physical separation steps (e.g., filtration may be avoided using two liquid phases to proceed with the reaction). As shown in FIG. 4, reactant 23 is functionalized by attachment of soluble form of precipiton 21a resulting in a reactant-precipiton complex or conjugate 25. This reactant-precipiton complex 25 is processed in solvent A through reaction 1 where the "X" functional group is replaced by functional group "Z". If there are contaminants in solvent A the intermediate-precipiton 27a is isomerized to shift the intermediate-precipiton complex out of solvent A in the form of an insoluble product-precipiton complex 29a. Insoluble product-precipiton complex 29a can be dissolved in a second solvent which may exist side-by-side in a two-phase system as shown in FIG. 3 or by liquid extraction. Solvent B is used as a solvent for isomerization of product-precipiton complex 29a which results in transformation back to the first intermediate-precipiton complex 27a. The value in this step is that any contaminants located in solvent A can be removed while the product-precipiton complex 29a is in solvent B. Essentially the product-precipiton complex 29a is isomerized back to the cis form resulting in intermediate-precipiton complex 27a which is utilized for reaction 2 wherein there is an alkene substitution of W on the alkene-functionalized portion of intermediate-precipiton complex 27a. Again, by selective manipulation of the precipiton portion of this intermediate-precipiton complex 27b, a second product-precipiton complex 29b which has a precipiton portion and includes the Z functional group as well as the W functional group can be isolated from solvent A. If the solvents exist side-by-side in a multi-phase system, phase shift or transfer can be used rather than collecting by filtration second product-precipiton complex 29b. In other words, product-precipiton complex 29b can be directly dissolved into solvent B. Second product-precipiton complex 29b can then be dissolved in solvent B and the precipiton portion of the product-precipiton complex 29b can be cleaved in solvent B resulting in the trans form of the precipiton being isolated in solvent B and the desired end product 31 being isolated in solvent A.

As briefly mentioned above, stilbenes appear to be particularly well suited as precipitons for purposes of the present invention. As will be described in greater detail below, a number of stilbenes were synthesized and tested for their suitability.

Napthylstilbenes (Scheme 1)

(2-Naphthalenylmethyl)triphenylphosphonium bromide ((a) Tinnemans, A. H. A.; Laarhoven, W. H. J. Chem. Soc. Perkin. Trans. 2, 1976, 1104–1111. (b) Zelikovich, L.; Hoffman, R. E.; Ayalon, A.; Rabinovitz, M. J. Chem. Soc. Perkin. Trans. 2, 1992, 1785–1792) was treated with NaH in DMF to generate a corresponding ylide. A solution of 4-methoxy-1-naphthaldehyde in DMF was added and stirred at 35–50° C. for 2 h at to give 1,2-naphthylstilbene 53 in 51% yield (53Z:53E=1:1.2). 6-Methoxy-2-naphthaldehyde ((a) Harvey, R. G.; Cortez, C.; Sawyer, T. W.; DiGiovanni, J.; J. Med. Chem. 1988, 31, 1308–1312. (b) Harvey, R. G.; Cortez, C. Tetrahedron, 1997, 53, 7101–7118) was prepared by formylation (Beringer, F. M.; Nathan, R. A. J. Org. Chem. 1969, 34, 685–689) of 6-methoxy-2-bromonaphthalene in 53% yield. When (2-naphthalenylmethyl)-triphenylphosphonium bromide was reacted with 6-methoxy-2-naphthaldehyde in a similar manner as 1,2-naphthylstilbene, (Z)-2,2-naphthylstilbene 54Z was prepared in 39% isolated yield. $R_f$ 0.44 (Hexanes/EtOAc 9/1); mp 140–142° C.; IR (KBr) 2997, 1624, 1600, 1501, 1481, 1389, 1269, 1248, 1032 cm$^{-1}$; $^1$H NMR (300 MHz, CDCl$_3$) δ7.79–7.34 (m, 11 H), 7.12–7.09 (m, 2 H), 6.8 (s, 2 H), 3.92 (s, 3 H); $^{13}$C NMR (75 MHz, CDCl$_3$) δ157.78, 135.04, 133.75, 133.44, 132.55, 130.58, 129.73, 129.48, 128.82, 128.01, 127.93, 127.59, 127.46, 126.99, 126.33, 125.98, 125.84, 118.80, 105.65, 55.26; HRMS calcd for C23H18O 310.1358, found 310.1361. There was also obtained a very insoluble solid, which is thought to be (E)-2,2-isomer 54E, but was not fully characterized because of its poor solubility.

Scheme 2

TBS-protected 2,2-naphthylstilbene TBS-protected naphthaldehyde 55 was prepared from 6-bromo-2-naphthol by

TBS protection (Wallimann, P.; Mattei, S.; Seiler, P.; Diederich, F. Helv. Chim. Acta. 1997, 80, 2368–2390) followed by formylation using DMF as a formylating reagent in 81% overall yield over 2 steps. The Wittig reaction of (2-naphthalenylmethyl)-triphenylphosphonium bromide with naphthaldehyde 55 using KHMDS base gave 2,2-naphthylstilbene 56 in 81% yield (56Z:56E=1:7.1).

Scheme 3

Phenolic stilbene 57Z was obtained via a route employing a TBS-protecting group (Scheme 3). TBS-protected benzylic bromide 58 (Giral, L.; Montginoul, C.; Schue, R. S. et F. Bull. Soc. Chim. Belg. 1990, 99, 147–166) was prepared in 2 steps by TBS protection (Stern, A. J.; Swenton, J. S. J. Org. Chem. 1989, 54, 2953–2958) and NBS bromination. Phosphonium bromide 59 (Giral, L.; Montginoul, C.; Schue, R. S. et F. Bull. Soc. Chim. Belg. 1990, 99, 147–166) was prepared by two different methods: In one method, a neat mixture of benzylic bromide 58 and PPh$_3$ was heated to melt with a heat gun for a few minutes to complete the reaction. (Stern, A. J.; Swenton, J. S. J. Org. Chem. 1989, 54, 2953–2958.) The second method was heating up the reaction mixture of benzylic bromide 58 and PPh$_3$ at 80–90° C. in THF over 6 hours.

The Wittig reaction of 4-biphenylcarboxaldehyde with the phosphonium ylide generated from the phosphonium bromide 59 by the deprotonation using KHMDS provided the TBS protected stilbene 60Z in 44% yield. Desilylation with tetra-n-butylammonium fluoride (TBAF) (Corey, E. J.; Venkateswarlu, A. J. Am. Chem. Soc. 1972, 94, 6190–6191) in THF afforded phenol 57Z in quantitative yield. R$_f$0.24 (Hexanes/CH$_2$Cl$_2$ 1/1); mp 97–103° C.; IR (KBr) 3530, 1608, 1508, 1485, 1255, 1171 cm$^{-1}$; $^1$H NMR (300 MHz, CDCl$_3$) δ7.61 (d, 2 H, J=7.3 Hz), 7.51–7.30 (m, 7 H), 7.21 (d, 2 H, J=8.5 Hz), 6.72 (d, 2 H, J=8.5 Hz), 6.55 (AB q, 2 H, J=12.6 Hz); $^{13}$C NMR (75 MHz, CDCl$_3$) δ154.55, 140.64, 139.52, 136.46, 130.35, 129.81, 129.24, 128.74, 128.41, 127.23, 126.84, 126.81, 115.11; HRMS calcd for C$_{20}$H$_{16}$O 272.1201, found 272.1201.

Table 1 illustrates the observed UV spectra of stilbene compounds (56Z, 56E, 60Z, 60E).

TABLE 1

| Stilbenes | λmax (nm) | ε (cm$^{-1}$mol$^{-1}$L) | conc'n (mM, THF) |
|---|---|---|---|
| 60Z | 304 | 19,600 | 0.114 |
| 60E | 332 | 47,500 | 0.0471 |
| 56Z | 320 | 18,900 | 0.143 |
| 56E | 339 | 40,300 | 0.0485 |

The E-stilbene isomer shows longer absorption maxima ($\lambda_{max}$) and stronger absorption coefficient ($\epsilon$) than the corresponding Z-isomer.

The phenolic or naphtholic group can be functionalized by attaching an acryloyl group (see Scheme 4 below).

The biphenyl stilbene 57Z was treated with NaH followed by acryloyl chloride to give stilbene 61Z in 68% yield. Naphthyl stilbene 62Z was prepared in 73% yield by desilylation followed by in-situ trapping of naphthoate anion with acryloyl chloride.

Illustrative Reactions Utilizing Precipitons i. Dipolar Additions

The 1,3-dipolar cycloaddition of stilbene 62Z with t-butyl nitrile oxide was carried out as seen in Scheme 5 below. t-Butyl chloro oxime was reacted with triethyl amine to generate t-butyl nitrile oxide in Et$_2$O solvent. A solution of stilbene 62Z in THF was treated with a t-butyl nitrile oxide solution at 30–40° C. for 2 h to complete the reaction.

The chemical isomerization using Ph$_2$S$_2$ gave 65E with a reasonably good yield of 55–62%.

ii. [4+2]-Diels-Alder Reaction

The diene used in our Diels-Alder reaction was cyclopentadiene and the dienophiles use were acrylate stilbenes (61Z and 62Z) (Scheme 6 and 7).

Scheme 6

In an analogous way, Diels-Alder reaction of stilbene 62Z followed by isomerization with Ph₂S₂, afforded the product 67E in an excellent 94% yield (see Scheme 7 below).

Scheme 7

The Diels-Alder reaction of acyl stilbene 61Z with 10 equiv of cyclopentadiene in THF gave (Z)-norbonene product 66Z. Beyond the desired products the a crude product mixture containing excess cyclopentadiene, cyclopentadiene byproducts, and other components of the reaction mixture such as solvent, unidentified reaction byproducts, and other contaminants. The reaction was followed by $^1$H nmr and the reaction was usually completed in 2 days. The isomerization was effected in the same manner as that for the [3+2] cycloaddition reaction. The photochemical isomerization with an UV light of 350 nm gave the (E)-norbonene product 66E in a relatively low 13% yield, whereas the chemical isomerization employing Ph₂S₂ provided the (E)-norbonene product 66E in excellent 78% yield. The disulfide induces isomerization of the precipiton and product precipitation. Filtration and washing of the precipitate provided product 66E in 78% yield and greater than 95% purity. The Ester was also treated with tert-butylnitrile oxide to afford, after isomerization and filtration, a cyclo adduct in 56% yield. The target moieties may be separated from the precipiton by dissolving the precipitate in a better solvent and cleaving the precipiton from the target. For example, (E) norbene product can be treated in MeOH/K2CO3 to provide the methyl ester. Evaporation of solvent and washing the residue with ether provide pure methyl ester (in solution) and recovered isomerized precipiton as a insoluble residue.

iii. 1,4-Michael Addition Reaction

The Michael addition of thio-nucleophiles on the solid-support has been carried out either to make small-compound libraries (Scheme 31) (Chen, C.; Randall, L. A. A.; Miller, R. B.; Jones, A. D.; Kurth, J. Am. Chem. Soc. 1994, 116, 2661–2662) or to discover potent inhibitors of matrix metalloproteinases or phosphodiesterases (Burns, C. J.; Groneberg, R. D.; Salvino, J. M.; McHeehan, G.; Condon, S. M.; Morris, R.; Morrissette, M.; mathew, R.; Darnbrough, S.; Neuenschwander, K.; Scotese, A.; Djuric, S. W.; Ullrich, J.; Labaudiniere, R. Angew. Chem. Int. Ed. Engl. 1998, 37, 2848–2850).

The trityl-ether connected polystyrene support (2% divinyl benzene-stryrene copolymer) with Michael acceptor reacted with thiophenols to give Michael addition products. The products were isolated by formic acid treatment.

The 1,4-Michael addition of thiophenols into acyl stilbenes (61Z and 62Z) was also performed (Schemes 8 and 9).

Scheme 8

A solution of acyl stilbene 61Z in THF was treated with either thiophenol or, 4-chlorothiophenol in the presence of catalytic amount of $Et_3N^{58}$ to give intermediate adducts (68Z and 69Z). The intermediate (Z)-product then underwent chemical isomerization with $Ph_2S_2$ to provide (E)-product 68E with thiophnol and 69E with 4-chlorothiophenol) in 83% and 76% isolated yield, respectively.

68E (83%, ArSH = thiophenol)
69E (76%, ArSH = 4-Cl thiophenol)

The Michael addition of thiophenol into acyl stilbene 62Z was carried out in the same fashion with 61Z (Scheme 10). The chemical isomerization with $Ph_2S_2$ to provided (E)-product (70E) in an excellent 93% yield.

Isolation of the Products by Methanolysis

The products can be, and in this case were isolated by methanolysis of the precipiton-attached products (68E, 69E, and 70E) (Scheme 34). A suspension of starting materials (68E, 69E, and 70E) in $CHCl_3$ was treated with methanolic HCl (generated in-situ from acetyl chloride with methanol). Upon completion of the methanolysis, the volatiles were evaporated. When the residue was treated with $Et_2O$, precipitons (57E or, 63E) were precipitated and filtered off to give 57E (88–100%) or, 63E (82%), respectively. The supernatant contains methyl ester products and evaporation of $Et_2O$ afforded methyl ester 71 (Shi, D.; Lu, Z.; Mu, L.; Dai, G. Synth. Commun. 1998, 28, 1073–1078) (100% from 68E, 61% from 70E) or, 72 (100%), respectively.

Scheme 9

Scheme 10

The present invention is directed to phase partitioning agents and the use of these agents and their analogs under various reactions. Although the invention has been described in detail and with reference to specific embodiments thereof, it will be apparent to those of ordinary skill in the art that various changes and modifications can be made therein without departing from the spirit and scope thereof.

What is claimed is:

1. A method of separating a desired product from a reaction mixture, said method comprising:
   covalently linking a separating agent to a reactant;
   reacting said reactant molecule to form a product, said separating agent being attached to said product;
   isomerizing said separating agent to thereby form a separable form of said product; and
   separating said product from said reaction mixture.

2. The method of claim 1, further including the step of cleaving said separating agent from said product to thereby form a purified product.

3. The method of claim 1, wherein said step of isomerizing is geometrical isomerization.

4. The method of claim 1, wherein said step of isomerizing is stereoisomerization.

5. The method of claim 1, wherein said step of isomerizing is structural isomerization.

6. The method of claim 1 wherein said modified reactant molecule may be selectably transferred from one phase (e.g., hydrophobic) to another (e.g., hydrophilic) by isomerization.

* * * * *